United States Patent
Konishi et al.

(10) Patent No.: US 9,506,091 B2
(45) Date of Patent: Nov. 29, 2016

(54) METHOD FOR PRODUCING GLUCARIC ACID

(71) Applicant: Asahi Kasei Chemicals Corporation, Tokyo (JP)

(72) Inventors: Kazunobu Konishi, Tokyo (JP); Shinichi Imazu, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 3 days.

(21) Appl. No.: 14/377,559

(22) PCT Filed: Feb. 19, 2013

(86) PCT No.: PCT/JP2013/053958
§ 371 (c)(1),
(2) Date: Aug. 8, 2014

(87) PCT Pub. No.: WO2013/125509
PCT Pub. Date: Aug. 29, 2013

(65) Prior Publication Data
US 2015/0010969 A1    Jan. 8, 2015

(30) Foreign Application Priority Data
Feb. 24, 2012   (JP) ................................. 2012-039129

(51) Int. Cl.
*C12N 9/16* (2006.01)
*C12P 7/58* (2006.01)

(52) U.S. Cl.
CPC . *C12P 7/58* (2013.01); *C12N 9/16* (2013.01); *C12Y 301/03025* (2013.01); *Y02P 20/52* (2015.11)

(58) Field of Classification Search
None
See application file for complete search history.

(56) References Cited

U.S. PATENT DOCUMENTS

2011/0124065 A1   5/2011   Moon et al.

FOREIGN PATENT DOCUMENTS

JP   2011-516063 A   5/2011
WO   2009-145838 A2  12/2009

OTHER PUBLICATIONS

Lee et al., Microbial production of building block chemicals and polymers., Current Opinion in biotechnology (2011), vol. 22, pp. 758-797.*
Branden and Tooze, Introduction to Protein Structure (1999), 2nd edition, Garland Science Publisher, pp. 3-12.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Extended European Search Report issued in counterpart European Patent Application No. 13751346.1 dated May 15, 2015.
Chen et al., "Overexpression, Purification, and Analysis of Complementation Behavior of E. coli SuhB Protein: Comparison with Bacterial and Archaeal Inositol Monophosphatases," Biochemistry, 39: 4145-4153 (2000).
Inada et al., "Lethal double-stranded RNA processing activity of ribonuclease III in the absence of SuhB protein of *Escherichia coli*," Biochimie, 77: 294-302 (1995).
Matsuhisa et al., "Inositol Monophosphatase Activity from the *Escherichia coli* suhB Gene Product," Journal of Bacteriology, 177: 200-205 (1995).
Moon et al., "Production of Glucaric Acid from a Synthetic Pathway in Recombinant *Escherichia coli*," Applied and Environmental Microbiology, 75: 589-595 (2009).
Moon et al., "Use of modular, synthetic scaffolds for improved production of glucaric acid in engineered *E. coli*," Metabolic Engineering, 12: 298-305 (2010).
Werpy et al., "Top Value Added Chemicals from Biomass vol. 1—Results of Screening for Potential Candidates from Sugars and Synthesis Gas," U.S. Department of Energy: Energy Efficiency and Renewable Energy, http://www1.eere.energy.gov/biomass/pdfs/35523.pdf (2004).
Office Action issued in counterpart Taiwanese Patent Application No. 10321025490 dated Jul. 28, 2014.
International Search Report issued in corresponding International Patent Application No. PCT/JP2013/053958 dated Mar. 19, 2013.

* cited by examiner

*Primary Examiner* — Alexander Kim
(74) *Attorney, Agent, or Firm* — Morgan, Lewis & Bockius LLP

(57) ABSTRACT

The disclosure provides a method for creating a transformant having significantly improved glucaric acid-producing capability and a method for efficiently producing glucaric acid using the transformant.

3 Claims, 3 Drawing Sheets

Figure 1

```
ATGACAGAAG ATAATATTGC TCCAATCACC TCCGTTAAAG TAGTTACCGA CAAGTGCACG
TACAAGGACA ACGAGCTGCT CACCAAGTAC AGCTACGAAA ATGCTGTAGT TACGAAGACA
GCTAGTGGCC GCTTCGATGT CACGCCCACT GTTCAAGACT ACGTGTTCAA ACTTGACTTA
AAAAAGCCGG AAAAACTAGG AATTATXCTC ATTGGGTTAG GTGGCAACAA TGGCTCCACC
TTAGTGGCCT CGGTATTGGC GAATAAGCAC AATGTGGAGT TTCAAACTAA GGAAGGCGTT
AAGCAACCAA ACTACTTCGG CTCCATGACT CAATGTTCTA CCTTGAAACT GGGTGTCGAT
GCGGAGGGGA ATGACGTTTA TGCTCCTTTT AACTCTCTGT TGCCCATGGT TAGCCCAAAC
GACTTTGTCG TCTCTGGTTG GGACATCAAT AACGCAGATC TATACGAAGC TATGCAGAGA
AGTCAGGTTC TCGAATATGA TCTGCAACAA CGCTTGAAGG CGAAGATGTC CTTGGTGAAG
CCTCTTCCTT CCATTTACTA CCCTGATTTC ATTGCAGCTA ATCAAGATGA GAGAGCCAAT
AACTGCATCA ATTTGGATGA AAAAGGCAAC GTAACCACGA GGGGTAAGTG GGCCCATCTG
CAACGCATCA GACGCGATAT TCAGAATTTC AAAGAAGAAA ACGCCCTTGA TAAAGTAATC
GTTCTTTGGA CTCCAAATAC TGAGAGGTCA GTAGAAGTAT CTCCTGGTGT TAATGACACC
ATGGAAAACC TCTTGCAGTC TATTAAGAAT GACCATGAAG AGATTGCTCC TTCCACGATC
TTTGCAGCAG CATCTATCTT GGAAGGTGTC CCTATATTA ATGGTTCACC GCAGAATACT
TTTGTTCCCG GCTTGGTTCA GCTGGCTGAG CATGAGGGTA CATTCATTGC GGGAGACCAT
CTCAAGTCGG GACAAACCAA GTTGAAGTCT GTTCTGCCCC AGTTCTTAGT GGATGCAGGT
ATTAAACCGG TCTCCATTGC ATCCTATAAC CATTTAGGCA ATAATGACGG TTATAACTTA
TCTGGTCCAA AACAATTTAG GTCTAAGGAG ATTTCCAAAA GTTCTGTCAT AGATGACATC
ATCGGGTCTA ATGATATCTT GTACAATGAT AAACTGGGTA AAAAAGTTGA CCACTGCATT
GTCATTAAAT ATATGAAGCC CGTCGGGGAC TCAAAAGTGG CAATGGACGA GTATTACAGT
GAGTTGATGT TAGGTGGCCA TAACCGGATT TCCATTCACA ATGTTTGCGA AGATTCTTTA
CTGGCTACGC CCTTGATCAT CGATCTTTTA GTCATGACTG AGTTTTGTAC AAGAGTGTCC
TATAAGAAGG TGGACCCAGT TAAAGAAGAT GCTGGCAAAT TTGAGAACTT TTATCCAGTT
TTAACCTTCT TGAGTTACTG GTTAAAAGCT CCATTAACAA GACCAGGATT TCACCCGGTG
AATGGCTTAA ACAAGCAAAG AACCGCCTTA GAAAATTTTT TAAGATTGTT GATTGGATTG
CCTTCTCAAA ACGAACTAAG ATTCGAAGAG AGATTGTTGT AA (SEQ ID NO 1)
```

Figure 2

```
atgcatccgatgctgaacatcgccgtgcgcgcagcgcgcaaggcgggtaatttaattgcc
aaaactatgaaaccccggacgctgtagaagcgagccagaaaggcagtaacgattcgtg
accaacgtagataaagctgccgaagcggtgattatcgacacgattcgtaaatcttaccca
cagcacaccatcatcaccgaagaaagcggtgaacttgaaggtactgatcaggatgttcaa
tgggttatcgatccactggatggcactaccaactttatcaaacgtctgccgcacttcgcg
gtatctatcgctgttcgtatcaaaggccgcaccgaagtgctgtggtatacgatcctatg
cgtaacgaactgttcaccgccactcgcggtcagggcgcacagctgaacggctaccgactg
cgcggcagcaccgctcgcgatctcgacggtactattctggcgaccggcttcccgttcaaa
gcaaaacagtacgccactacctacatcaacatcgtcggcaaactgttcaacgaatgtgca
gacttccgtcgtaccggttctgcggcgctggatctggcttacgtcgctgcgggtcgtgtt
gacggtttctttgaaatcggtctgcgcccgtgggacttcgccgcaggcgagctgctggtt
cgtgaagcgggcggcatcgtcagcgacttcaccggtggtcataactacatgctgaccggt
aacatcgttgctggtaacccgcgcgttgttaaagccatgctggcgaacatgcgtgacgag
ttaagcgacgctctgaagcgttaa (SEQ ID NO 3)
```

Figure 3

```
         10         20         30         40         50         60
ATGAAAGTTG ATGTTGGTCC TGATCCGTCT CTGGTTTATC GTCCAGACGT GGATCCGGAG 70         80         90        100        110        120
ATGGCAAAGA GCAAAGACTC TTTCCGTAAC TACACTTCTG GTCCGCTGCT GGATCGCGTT 130        140        150        160        170        180
TTCACGACCT ACAAACTGAT GCACACCCAT CAGACCGTTG ATTTCCTGAG CCGCAAGCGC 190        200        210        220        230        240
ATCCAGTATG GTTCTTTCTC TTACAAAAAG ATGACCATTA TGGAGGCTGT TGGTATGCTG 250        260        270        280        290        300
GATGACCTGG TTGACGAAAG CGACCCTGAC GTTGACTTCC CTAACTCTTT CCATGCATTT 310        320        330        340        350        360
CAGACCGCCG AAGGTATTCG TAAAGCTCAT CCTGATAAAG ATTGGTTCCA CCTGGTCGGT 370        380        390        400        410        420
CTGCTGCACG ACCTGGGTAA GATCATGGCG CTGTGGGGCG AACCACAATG GGCCGTAGTC 430        440        450        460        470        480
GGCGATACTT TCCCGGTGGG CTGCCGCCCA CAGGCATCCG TGGTCTTCTG CGACTCTACC 490        500        510        520        530        540
TTCCAGGATA ACCCGGATCT GCAGGATCCG CGCTATTCCA CCGAACTGGG CATGTACCAG 550        560        570        580        590        600
CCGCATTGCG GCCTGGAGAA CGTTCTGATG TCTTGGGGTC ACGACGAGTA CCTGTATCAG 610        620        630        640        650        660
ATGATGAAAT TCAACAAATT CTCCCTGCCG TCCGAGGCAT TTACATGAT CCGTTTTCAC 670        680        690        700        710        720
TCCTTCTACC CGTGGCATAC CGGTGGCGAT TATCGTCAGC TGTGCTCTCA GCAGGATCTG 730        740        750        760        770        780
GATATGCTGC CGTGGGTTCA GGAATTCAAT AAATTCGACC TGTATACCAA ATGCCCTGAC 790        800        810        820        830        840
CTGCCAGATG TTGAATCCCT GCCGCCATAC TACCAAGGCC TGATTGACAA ATACTGCCCG 850        860
GGCACCCTGT GCTGGTAA   (SEQ ID NO 5)
```

Figure 4

```
         10         20         30         40         50         60
  atgaccacta cccccttcaa tcgcctgctg ctcaccggag ccgcaggcgg cctgggcaag 70         80         90        100        110        120
  gtccttcgcg aacgcctgaa aggctacggc gaggtcctgc gcctgtctga catcagcccc 130        140        150        160        170        180
  atggcccggc ccgcgggccc gcatgaagaa gtcattacct gtgacctggc cgacaaggct 190        200        210        220        230        240
  gcggtgcata ccctggtcga gggcgtagac gccatcatcc actttggcgg ggttctacc 250        260        270        280        290        300
  gaacacgcct tcgaagagat tctcggcccc aatatctgcg gcgtgttcca cgtgtacgag 310        320        330        340        350        360
  gcggcgcgca agcacggggt caagcgcatc atcttcgcca gtccaaacca caccatcggt 370        380        390        400        410        420
  ttctatcgcc aggatgagcg catcgacgct caacgcgcg gccggccga cagctattac 430        440        450        460        470        480
  gggctgtcca agtgctacgg cgaagatgtg gccagctct actttgaccg ctacggcatc 490        500        510        520        530        540
  gagaccgtca gcatcgcat cggctcgtcg ttcccgcagc cacagaaact gcgcatgctc 550        560        570        580        590        600
  tgcacctggc tcagttacga cgacctggtg cagttgatcg aacgcgggct gttcaccccc 610        620        630        640        650        660
  ggggttggcc acaccatcgt ctacggcgcc tccgacaatc gcaccgtgtg gtggacaac 670        680        690        700        710        720
  cgccatgccg cgcacctggg ctatgtaccc aaggacagct ccgaaaccit ccggcagcc 730        740        750        760        770        780
  gtggaggccc aaccggcacc cgccgccgat gaccggagca tggtctacca gggcggcgct 790        800        810
  ttcgccgtgg ccggccgtt caactga   (SEQ ID NO 7)
```

METHOD FOR PRODUCING GLUCARIC ACID

A computer readable text file, entitled "SequenceListing.txt," created on or about Aug. 7, 2014 with a file size of about 33 kb contains the sequence listing for this application and is hereby incorporated by reference in its entirety.

TECHNICAL FIELD

The present invention relates to the application of gene recombination technology in the production of glucaric acid.

BACKGROUND ART

Glucaric acid (tetrahydroxyadipic acid) is a compound discovered long ago in plants and mammals.

In a recent report on high value-added chemicals to be made from biomass (Non-patent Reference 1), the U.S. National Renewable Energy Laboratory listed glucaric acid among the top 12 compounds. This report gives glucaro-γ-lactone, glucaro-δ-lactone, glucarodilactone, and other such lactones (which can be expected to be used as solvents), polyhydroxypolyamides (which can be expected to be used as novel nylons), and the like as examples of glucaric acid derivatives that can be prepared using glucaric acid as a raw material. This report also states that nitric acid oxidation of starch and catalytic oxidation in the presence of basic bleach can be utilized as known methods of producing glucaric acid.

Patent Reference 1 also more recently disclosed transformants capable of biosynthesizing glucaric acid. Specifically, in Patent Reference 1, an *Escherichia coli* host was transfected by three genes encoding myo-inositol-1-phosphate synthase (Ino1), myo-inositol oxygenase (MIOX), and uronic acid dehydrogenase (udh). It states that the transformants obtained in this way produced glucaric acid in a concentration of 0.72-1.13 g/L in the medium. However, the inventors of Patent Reference 1 held that introduction of an inositol monophosphatase (suhB) gene into the transformants of this patent reference was unnecessary.

Specifically, five activities are theoretically required in a glucaric acid biosynthetic pathway using glucose as a substrate:

activity 1: activity to produce glucose-6-phosphate from a suitable carbon source;

activity 2: activity to convert glucose-6-phosphate into myo-inositol-1-phosphate, that is, inositol-1-phosphate synthase activity;

activity 3: activity to convert myo-inositol-1-phosphate into myo-inositol, that is, phosphatase activity taking myo-inositol-1-phosphate as a substrate activity 4: activity to convert myo-inositol into glucuronic acid, that is, myo-inositol oxygenase activity; and activity 5: activity to convert glucuronic acid into glucaric acid, that is, uronic acid dehydrogenase activity. However, since the glucose-6-phosphate that is a product of activity 1 is in fact a metabolic intermediate universally produced by prokaryotic microorganisms, it is not essential to impart this activity to prokaryotic microorganisms.

With regard to activity 3 as well, many microbial strains are known to express endogenous inositol monophosphatase or to have general monophosphatase activity capable of using myo-inositol-1-phosphate as a substrate. It is therefore understandable that no inositol monophosphatase gene was introduced into the transformants of Patent Reference 1.

Therefore, Patent Reference 1 concludes that an inositol monophosphatase gene need not be introduced into transformants to biosynthesize glucaric acid based on metabolic analysis of the transformants produced. Specifically, Patent Reference 1 states "It should also be noted that we did not overexpress the suhB gene or a homologous phosphatase. However, no myo-inositol-1-phosphate was detected among the culture products, while myo-inositol did accumulate. Therefore, we conclude that the phosphatase activity is not limiting flux through the pathway." (page 33, lines 2-5).

Therefore, there existed no obvious motivation for introducing an inositol monophosphatase gene into transformants for the biosynthesis of glucaric acid.

PRIOR ART REFERENCES

Patent References

Patent Reference 1: WO2009/145838 pamphlet

Non-Patent References

Non-patent Reference 1: Top Value Added Chemicals from Biomass Volume 1—Results of Screening for Potential Candidates from Sugars and Synthesis Gas, http://www1.eere.energy.gov/biomass/pdfs/35523.pdf, T. Werpy and G. Peterson, published August 2004.

SUMMARY OF THE INVENTION

Problems to be Solved by the Invention

The problem to be solved by the invention is the production of transformants having significantly improved glucaric acid production capacity and their utilization.

Means Used to Solve the Above-Mentioned Problems

As was discussed above, even Patent Reference 1 that disclosed transformants capable of biosynthesizing glucaric acid does not introduce an inositol monophosphatase gene into these transformants and paid no particular attention to this activity.

However, contrary to the expectations of Patent Reference 1, the present inventors discovered that inositol monophosphatase activity plays an important role in transformants for glucaric acid biosynthesis. Among other things, enhancing the inositol monophosphatase activity improves the glucaric acid production capacity of such transformants an astonishing several ten to several hundred-fold.

Therefore, the first aspect of the present invention is (1) A method for producing glucaric acid including the following steps:

1) a step preparing a transformant possessing an inositol-1-phosphate synthase gene, inositol monophosphatase gene, myo-inositol oxygenase gene, and uronic acid dehydrogenase gene, the transformant having a gene recombination or mutation to induce functional inositol monophosphatase overproduction or inositol monophosphatase activation within the transformant;

2) a step for bringing the transformant into contact with a carbon source that can be converted into glucaric acid by the transformant under conditions suited to growth and/or maintenance of the transformant; and 3) a step for separating the glucaric acid or glucarate from culture obtained in the step 2).

More specifically, it is a method for producing glucaric acid using a transformant possessing an inositol-1-phosphate synthase gene, inositol monophosphatase gene, myo-inositol oxygenase gene, and uronic acid dehydrogenase gene, the production method being characterized in that this transformant is a transformant having a gene recombination or mutation to induce functional inositol monophosphatase overproduction or inositol monophosphatase activation.

In the fermentative production of glucaric acid of the present invention, it is preferable to use a carbon source containing a compound suited to the production of glucose-6-phosphate, which is a substrate of inositol-1-phosphate synthase (the above-mentioned activity 2). Therefore, preferred embodiments of the present invention are:

(2) The production method according to (1) above, wherein the carbon source contains a compound that can be converted into glucose-6-phosphate within the transformant; and (3) The method according to (2) above, wherein the carbon source is one or more selected from the group consisting of D-glucose, sucrose, oligosaccharide, polysaccharide, starch, cellulose, rice bran, molasses, and biomass containing D-glucose.

Prokaryotic microorganisms typified by *Escherichia coli* are very attractive from the viewpoint of industrial fermentative production due to their rapid growth ability and ease of fermentation control and have advantages from the viewpoint of the practical accomplimeshment in the application of gene recombination techniques and the established safety. The many prokaryotic microorganisms that do not have a glucaric acid biosynthetic pathway from glucose via myo-inositol also have an advantage in ease of glucaric acid productivity by the use of synthetic biology techniques in cooperation with genetic recombination techniques. Prokaryotic microbial hosts such as *E. coli* in particular make the application of synthetic biology techniques even easier since they do not have the ability to assimilate (ability to decompose) myo-inositol, an intermediate of the glucaric acid biosynthetic pathway. Therefore, preferred embodiments of the present invention are:

(4) The production method according to any of (1) to (3) above, wherein the transformant is derived from a microorganism not having myo-inositol assimilation capacity; and (5) The production method according to any of (1) to (4) above, wherein the transformant is derived from a bacterium selected from the group consisting of *Escherichia coli*, bacteria belonging to the genus *Bacillus*, bacteria belonging to the genus *Corynebacterium*, and bacteria belonging to the genus *Zymomonas*.

Regardless of whether or not the host microorganism has endogenous inositol monophosphatase activity, inducing overproduction of inositol monophosphatase within the cell can enhance the inositol monophosphatase activity of the cell. Inositol monophosphatase overproduction can be induced in the cell by applying various known techniques. Therefore, the present invention includes the following embodiments:

(6) The production method according to any of (1) to (5) above, wherein the inositol monophosphatase overproduction is induced by, in the transformant:

a) introducing an exogenous inositol monophosphatase gene, b) increasing the number of copies of an endogenous inositol monophosphatase gene, c) introducing a mutation into a regulatory region of the endogenous inositol monophosphatase gene, d) replacing the regulatory region of the endogenous inositol monophosphatase gene with a high expression-inducing exogenous regulatory region, or e) deleting the regulatory region of the endogenous inositol monophosphatase gene; and (7) The production method according to (6) above, wherein the inositol monophosphatase overproduction is induced by introducing the exogenous inositol monophosphatase gene into the above transformant.

In addition, when the host cell has an endogenous inositol monophosphatase gene, the inositol monophosphatase activity of the cell can be enhanced by the following embodiments as well.

(8) The production method according to any of (1) to (5) above, wherein the inositol monophosphatase activation is induced by, in the transformant:

f) introducing a mutation into the endogenous inositol monophosphatase gene, g) replacing all or part of the endogenous inositol monophosphatase gene, h) deleting part of the endogenous inositol monophosphatase gene, i) reducing other proteins that lower inositol monophosphatase activity, or j) reducing production of compounds that lower inositol monophosphatase activity.

The present invention also intends transformants for use in the production method of glucaric acid. Therefore, the second aspect of the present invention is:

(9) A transformant possessing an inositol-1-phosphate synthase gene, inositol monophosphatase gene, myo-inositol oxygenase gene, and uronic acid dehydrogenase gene, the transformant having a gene recombination or mutation to induce functional inositol monophosphatase overproduction or inositol monophosphatase activation within the transformant.

More specifically, it is a transformant possessing an inositol-1-phosphate synthase gene, inositol monophosphatase gene, myo-inositol oxygenase gene, and uronic acid dehydrogenase gene, the transformant being characterized by having a gene recombination or mutation to induce functional inositol monophosphatase overproduction or inositol monophosphatase activation.

Embodiments mentioned with regard to the first aspect of the present invention are also true for the second aspect of the present invention. These embodiments include:

(10) The transformant according to (9) above, wherein the transformant is derived from a microorganism not having myo-inositol assimilation capacity;

(11) The transformant according to either (9) or (10) above, wherein the transformant is derived from a bacterium selected from the group consisting of *Escherichia coli*, bacteria belonging to the genus *Bacillus*, bacteria belonging to the genus *Corynebacterium*, and bacteria belonging to the genus *Zymomonas*;

(12) The transformant according to any of (9) to (11) above, wherein the inositol monophosphatase overproduction is induced by, in the transformant:

a) introducing an exogenous inositol monophosphatase gene, b) increasing the number of copies of an endogenous inositol monophosphatase gene, c) introducing a mutation into a regulatory region of the endogenous inositol monophosphatase gene, d) replacing the regulatory region of the endogenous inositol monophosphatase gene with a high expression-inducing exogenous regulatory region, or e) deleting the regulatory region of the endogenous inositol monophosphatase gene;

(13) The transformant according to (12) above, wherein the inositol monophosphatase overproduction is induced by introducing the exogenous inositol monophosphatase gene into the transformant; and

(14) The transformant according to any of (9) to (11) above, wherein the inositol monophosphatase activation is induced by, in the transformant:

f) introducing a mutation into the endogenous inositol monophosphatase gene, g) replacing all or part of the endogenous inositol monophosphatase gene, h) deleting part of the endogenous inositol monophosphatase gene, i) reducing other proteins that lower inositol monophosphatase activity, or j) reducing production of compounds that lower inositol monophosphatase activity.

Advantages of the Invention

The present invention makes it possible to achieve more efficient industrial glucaric acid production through microbial culture techniques.

BRIEF DESCRIPTION OF THE DRAWINGS

FIG. 1 shows a coding region of INO1 gene (SEQ ID NO:
FIG. 2 shows a coding region of suhB gene (SEQ ID NO: 3).
FIG. 3 shows a coding region of miox gene (SEQ ID NO: 5).
FIG. 4 shows a coding region of udh gene (SEQ ID NO: 7).

BEST MODE FOR CARRYING OUT THE INVENTION

The problem of the present invention is solved by enhancing the inositol monophosphatase activity in a transformant possessing an inositol-1-phosphate synthase gene, inositol monophosphatase gene, myo-inositol oxygenase gene, and uronic acid dehydrogenase gene.

The transformant of the present invention can be made using various host microbial cells. In particular, the use of prokaryotes as a host makes it possible to newly construct a glucaric acid biosynthetic pathway in the host cell (that is, without the effect of an existing endogenous pathway). This is extremely attractive for the application of synthetic biology techniques. Prokaryotic microorganisms that can be given as examples are bacteria belonging to the genera *Escherichia, Pseudomonas, Bacillus, Geobacillus, Methanomonas, Methylobacillus, Methylophilus, Protaminobacter, Methylococcus, Corynebacterium, Brevibacterium, Zymomonas*, and *Listeria*. Nonlimiting examples of prokaryotic microorganisms suited to industrial fermentative production include *Escherichia coli*, bacteria belonging to the genus *Bacillus*, bacteria belonging to the genus *Corynebacterium*, and bacteria belonging to the genus *Zymomonas*. *Escherichia coli* is an especially preferred example of a host microorganism of the present invention because of its rapid growth capacity and ease of fermentation control.

Cell lines that can be utilized as host cells of the present invention may be wild types in the ordinary sense or may be auxotrophic mutants or antibiotic-resistant mutants. Cell lines that can be utilized as host cells of the present invention may also be already transformed so as to have various marker genes related to the above mutations. These mutations and genes make it possible to provide properties beneficial to the production, maintenance, and control of the transformants of the present invention. Preferably, the use of a strain presenting resistance to chloramphenicol, ampicillin, kanamycin, tetracycline, and another such antibiotics makes it possible to produce the glucaric acid of the present invention easily.

In the present invention directed toward synthetic biology, when the host microorganism does not express endogenous inositol-1-phosphate synthase, an exogenous inositol-1-phosphate synthase gene is introduced to construct a new glucaric acid biosynthetic pathway in the host cell. Furthermore, in this specification, the term "exogenous" is used to mean that a gene or nucleic acid sequence based on the present invention is introduced into a host in a case in which the host microorganism prior to transformation does not have the gene to be introduced by the present invention, in a case in which it substantially does not express the enzyme encoded by this gene, and in a case in which the amino acid sequence of this enzyme is encoded by a different gene, but endogenous enzyme activity comparable to that after transformation is not expressed.

Inositol-1-phosphate synthase genes are known (for example, GenBank Accession Nos. AB032073, AF056325, AF071103, AF078915, AF120146, AF207640, AF284065, BC111160, L23520, U32511), and any of these can be used for the purposes of the present invention. An inositol-1-phosphate synthase gene having a coding region nucleotide sequence shown by SEQ ID NO: 1 in particular can be used preferably in the present invention. However, inositol-1-phosphate synthase genes that can be utilized in the present invention are not limited to the above and may be derived from other organisms or may be artificially synthesized, as long as they are capable of expressing substantial inositol-1-phosphase synthase activity within the host microbial cells.

Therefore, inositol-1-phosphate synthase genes that can be utilized for purposes of the present invention may have any mutations capable of occurring in the natural world and artificially introduced mutations and modifications as long as they are capable of expressing substantial inositol-1-phosphase synthase activity within the host microbial cells. For example, the presence of excess codons (redundancy) is known in various codons that encode specific amino acids. Alternate codons that are finally translated into the same amino acids may therefore also be utilized in the present invention. In other words, since the genetic code degenerates, multiple codons can be used to encode certain specific amino acids, and the amino acid sequence can therefore be encoded by a DNA oligonucleotide similar to any one set. While only one member of that set is identical to the genetic sequence of the native enzyme, even mismatched DNA oligonucleotides can hybridize with the native sequence under suitable stringent conditions (for example, hybridization by 3×SSC, 68° C.; washing by 2×SSC, 0.1% SDS, and 68° C.), and DNA that encodes the native sequence can be identified and isolated. Such genes can also be utilized in the present invention. In particular, since virtually all organisms are known to use subsets of specific codons (optimal codons) preferentially (Gene, Vol. 105, pp. 61-72, 1991, and the like), "codon optimization" in accordance with the host microorganism can also be useful in the present invention.

Those skilled in the art will appreciate that a more stable, higher level of inositol-1-phosphate synthase activity can be obtained, in the present invention as well, by introducing an inositol-1-phosphate synthase gene into the host microbial cell as an "expression cassette." In this specification, "expression cassette" means a nucleotide containing a nucleic acid sequence that regulates transcription and translation functionally linked to the nucleic acid to be expressed or the gene to be expressed. Typically, an expression cassette of the present invention contains a promoter sequence 5' upstream from the coding sequence, a terminator sequence 3' downstream from the sequence. Sometimes it contains a further normal regulatory element in a functionally linked state. In such cases, the nucleic acid to be expressed or the gene to be expressed is "introduced expressibly" into the host microorganism.

A promoter is defined as a DNA sequence that links RNA polymerase to DNA and initiates RNA synthesis, regardless of whether it is a constitutive promoter or a regulatory promoter. A strong promoter means a promoter that initiates mRNA synthesis at high frequency and is also preferably used in the present invention. A lac promoter, trp promoter, TAC or TRC promoter, major operator and promoter regions of λ phage, fd coat protein control region, promoters for a glycolytic enzymes (for example, 3-phosphoglycerate kinase, glyceraldehyde-3-phosphate dehydrogenase), glutamate decarboxylase A, serine hydroxymethyl transferase, and the like can be utilized in accordance with the properties and the like of the host cells. In addition to promoter and terminator sequences, examples of regulatory elements include selection markers, amplification signals, replication origins, and the like. Suitable regulatory sequences are listed, for example, in "Gene Expression Technology: Methods in Enzymology 185," Academic Press (1990).

The expression cassette explained above is incorporated, for example, into a vector consisting of a plasmid, phage, transposon, IS element, phasmid, cosmid, linear or circular DNA, or the like, and inserted into the host microorganism. Plasmids and phages are preferred. These vectors may be autonomously replicated in the host microorganism or may be replicated chromosomally. Suitable plasmids include, for example, *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, λgt11 or pBdCI; *Bacillus* pUB110, pC194 or pBD214; *Corynebacterium* pSA77 or pAJ667; and the like. Plasmids and the like that can also be used in addition to these are listed in "Cloning Vectors," Elsevier, 1985. The expression cassette can be introduced into the vector by ordinary methods, including excision by suitable restriction enzymes, cloning, and ligation.

After having constructed a vector having an expression cassette of the present invention as discussed above, coprecipitation, protoplast fusion, electroporation, retrovirus transfection, and other such ordinary cloning methods and transfection methods are used as methods that can be used to introduce the vector into the host microorganism. Examples of these are listed in "Current Protocols in Molecular Biology," F. Ausubel et al., Publ. Wiley Interscience, New York, 1997 or Sambrook et al., "Molecular Cloning: Laboratory Manual," 2$^{nd}$ edition, Cold Spring Harbor Laboratory, Cold Spring Harbor Laboratory Press, Cold Spring Harbor, N.Y., 1989.

Surprisingly enough, the present inventors discovered that inositol monophosphatase activity plays an important role in transformants obtained by introducing a glucaric acid biosynthetic pathway into a host microorganism not having an endogenous glucaric acid biosynthetic pathway. As was mentioned above, none of the research conducted up to this point paid any particular attention to inositol monophosphatase activity. However, enhancing the inositol monophosphatase activity unexpectedly greatly improved the glucaric acid production capacity of such transformants.

Therefore, one embodiment of the present invention encompasses inducing overproduction of inositol monophosphatase in transformants possessing an inositol-1-phosphate synthase gene, inositol monophosphatase gene, myo-inositol oxygenase gene, and uronic acid dehydrogenase gene.

The inositol monophosphatase intended in the present invention includes proteins capable of substantially hydrolyzing inositol-1-phosphate by presenting phosphoric monoester hydrolase activity capable of acting on a wide range of substrates in addition to those presenting high substrate specificity for inositol-1-phosphate. For example, inositol-1-monophosphatase is known as a typical inositol monophosphatase, and this gene (suhB gene) from many organisms has been published in GenBank Accession Nos. ZP_04619988, YP_001451848, and the like. The use of a suhB gene from *E. coli* (SEQ ID NO: 3: AAC75586 (MG1655)) is especially convenient when *E. coli* is used as the host cell.

The next bioactivity that the transformant of the present invention should have is myo-inositol oxygenase activity. This enzyme typically converts myo-inositol into glucuronic acid by the following reaction.

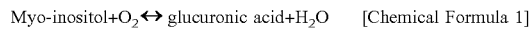

Myo-inositol+$O_2$ ↔ glucuronic acid+$H_2O$ [Chemical Formula 1]

Various myo-inositol oxygenase genes are known and can be utilized. For example, WO2002/074926 pamphlet discloses myo-inositol oxygenase genes derived from *Cryptococcus* and humans and heterologous expression thereof. In addition, the myo-inositol oxygenase genes disclosed in Patent Reference 1 can be used in the present invention. The following myo-inositol oxygenase genes derived from many organisms to which the following GenBank Accession numbers have been assigned, for example, are also useful in the present invention.
ACCESSION No. AY738258 (*Homo sapiens* myo-inositol oxygenase (MIOX))
ACCESSION No. NM101319 (*Arabidopsis thaliana* inositol oxygenase 1 (MIOX1))
ACCESSION No. NM001101065 (*Bos taurus* myo-inositol oxygenase (MIOX))
ACCESSION No. NM001030266 (*Danio rerio* myo-inositol oxygenase (miox))
ACCESSION No. NM214102 (*Sus scrofa* myo-inositol oxygenase (MIOX))
ACCESSION No. AY064416 (*Homo sapiens* myo-inositol oxygenase (MIOX))
ACCESSION No. NM001247664 (*Solanum lycopersicum* myo-inositol oxygenase (MIOX))
ACCESSION No. XM630762 (*Dictyostelium discoideum* AX4 inositol oxygenase (miox))
ACCESSION No. NM145771 (*Rattus norvegicus* myo-inositol oxygenase (Miox))
ACCESSION No. NM017584 (*Homo sapiens* myo-inositol oxygenase (MIOX))
ACCESSION No. NM001131282 (*Pongo abelii* myo-inositol oxygenase (MIOX))

It is especially convenient to use a miox gene having a coding region nucleotide sequence shown by SEQ ID NO: 5.

The final bioactivity that the transformed microorganism of the present invention should have is uronic acid dehydrogenase activity. This enzyme typically converts glucuronic acid into glucaric acid in the presence of NAD$^+$ by the following reaction.

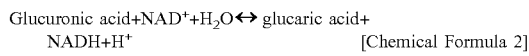
NADH+H$^+$ [Chemical Formula 2]

Various uronic acid dehydrogenase genes are known and can be utilized. For example, uronic acid dehydrogenase from *Pseudomonas aeruginosa* and bacteria belonging to the genus *Agrobacterium* disclosed in Patent Reference 1 can also be used in the present invention. The udh genes to which the following GenBank Accession numbers have been assigned, for example, are also useful in the present invention.
ACCESSION No. BK006462 (*Agrobacterium tumefaciens* str. C58 uronate dehydrogenase (udh) gene)
ACCESSION No. EU377538 (*Pseudomonas syringae* pv. tomato str. DC3000 uronate dehydrogenase (udh) gene)

It is especially convenient to use a udh gene having a coding region nucleotide sequence shown by SEQ ID NO: 7.

Those skilled in the art will readily appreciate that all the above explanation of mutation, modification, and codon optimization, expression cassette, promoter and other regulator sequences and plasmids, and transformation thereby given with regard to the inositol-1-phosphate synthase gene holds true for the inositol monophosphatase genes, myo-inositol oxygenase genes, and uronic acid dehydrogenase genes of the present invention. Therefore, the transformants of the present invention can possess four expression cassettes: an expression cassette containing nucleic acid that encodes inositol-1-phosphate synthase, an expression cassette containing nucleic acid that encodes an inositol monophosphatase gene, an expression cassette containing nucleic acid that encodes myo-inositol oxygenase, and an expression cassette containing nucleic acid that encodes uronic acid dehydrogenase. Preferred transformants of the present invention possess an expression cassette containing nucleic acid having a nucleotide sequence shown by SEQ ID NO: 1, an expression cassette containing nucleic acid having a nucleotide sequence shown by SEQ ID NO: 3, an expression cassette containing nucleic acid having a nucleotide sequence shown by SEQ ID NO: 5, and an expression cassette containing nucleic acid having a nucleotide sequence shown by SEQ ID NO: 7.

These four expression cassettes may be placed on one vector and transfected into a host microorganism. Alternatively, a vector on which any two or more of the expression cassettes are placed and a vector on which the remaining expression cassettes are placed may be co-transfected into a host microorganism, or four vectors, each with an expression cassette, may be co-transfected into a host microorganism. Furthermore, any one or more of the above four expression cassettes may be incorporated into the genome of a host microorganism, and the remaining expression cassettes may be present as plasmids within the transformed microorganism. For example, a plasmid having an expression cassette containing nucleic acid that encodes myo-inositol oxygenase and an expression cassette containing nucleic acid that encodes uronic acid dehydrogenase can also be transfected into *E. coli* AKC-018 (deposited as FERM P-22181 on Oct. 25, 2011 at the Incorporated Administrative Agency National Institute of Technology and Evaluation, Patent Micoorganisms Depositary. International accession number: FERM BP-11514) having both an expression cassette containing inositol-1-phosphate synthase encoding nucleic acid (INO1) and an expression cassette containing nucleic acid encoding inositol monophosphatase (suhB) on a chromosome.

Furthermore, many microbial cells are known to express the inositol monophosphatase activity (that is, to have an endogenous gene that encodes inositol monophosphatase activity) intended in the present invention. Therefore, overproduction of inositol monophosphatase can also be induced in the present invention by increasing the number of copies of an endogenous inositol monophosphatase gene; introducing a mutation into a regulatory region of an endogenous inositol monophosphatase gene; replacing a regulatory region of an endogenous inositol monophosphatase gene with a high expression-inducing exogenous regulatory region; and deleting a regulatory region of an endogenous inositol monophosphatase gene. Specifically, overexpression of inositol monophosphatase can be achieved by transforming the above-mentioned host microorganism by a construct containing an endogenous inositol monophosphatase gene or an expression cassette having a suitable regulatory region added to the region that encodes this endogenous gene, thereby substantially increasing the number of copies of the inositol monophosphatase gene in the transformant in comparison to that of the original host cell; mutating, adding, and deleting chromosomes with regard to an original host cell having an endogenous inositol monophosphatase gene by known genetic recombination techniques; or introducing mutations randomly into the chromosomes using a mutagen or the like. Overproduction of inositol monophosphatase can be confirmed by using known SDS-PAGE analytical methods, and the like.

Another embodiment of the present invention to enhance the inositol monophosphatase activity includes inducing activation of inositol monophosphatase in the above-mentioned host microbial cells. Examples of techniques used for this purpose include 1) introduction of mutation into an endogenous inositol monophosphatase gene, 2) partial or complete replacement of an endogenous inositol monophosphatase gene, 3) partial deletion of an endogenous inositol monophosphatase gene, 4) reduction of the quantity of other proteins that lower inositol monophosphatase activity, and/or 5) reduction of production of compounds that lower inositol monophosphatase activity.

With regard to the above methods 1)-5) to enhance inositol monophosphatase activity, inositol monophosphatase having enhanced inositol monophosphatase activity can be obtained by evaluating the activity of inositol monophosphatase encoded by this gene after having subjected the inositol monophosphatase gene to mutation, addition, or deletion.

The transformants obtained as described above are cultured and maintained under conditions suited to the growth and/or maintenance of the transformants to produce the glucaric acid of the present invention. Suitable medium compositions, culture conditions, and culture times for transformants derived from various host microbial cells are known to those skilled in the art.

The medium may be natural, semisynthetic, or synthetic medium containing one or more carbon sources, nitrogen sources, inorganic salts, vitamins, and, sometimes, trace elements or vitamins, and other such trace components. However, it goes without saying that the medium used must properly satisfy the nutrient requirements of the transformants to be cultured. To bring the transformant into contact with a carbon source that can be converted into glucaric acid by the transformant, the medium of the present invention should contain a carbon source that can ultimately be utilized as a substrate for glucaric acid production, that is, a compound that can be converted into glucose-6-phosphate within the transformant. The carbon source can be D-glucose, sucrose, oligosaccharide, polysaccharide, starch, cellulose, rice bran, or molasses, or a biomass containing D-glucose. Examples of suitable biomasses include decomposed corn solution and decomposed cellulose solution. When the transformants express useful additional traits, for example, when they have resistance markers for antibiotics, the medium may contain the corresponding antibiotics. This reduces the risk of contamination by foreign bacteria during fermentation.

When the host microorganisms cannot assimilate cellulose, polysaccharides, or another such carbon source, the host microorganisms can be adapted to glucaric acid production using these carbon sources by introducing an exogenous gene or other such known genetic engineering techniques. Examples of exogenous genes include cellulase genes, amylase genes, and the like.

Culture may be either by batch or continuous. In either case, it may be in the form of supplying additional abovementioned carbon source and the like at a suitable point in time during culture. Culture should also be continued while maintaining a suitable temperature, oxygen concentration, pH, and the like. A suitable culture temperature for transformants derived from common microbial host cells is usually in the range of 15-45° C., preferably 25-37° C. When the host microorganism is aerobic, shaking (flask culture and the like), stirring/aeration (jar fermenter culture and the like) is necessary to assure a suitable oxygen concentration during fermentation. These culture conditions are easy to establish for those skilled in the art.

Methods known to those skilled in the art can be combined to refine glucaric acid from the above culture. For example, useful methods of detecting and assaying glucaric acid for this purpose are described concretely in Patent Reference 1.

Those skilled in the art who have been provided with the above explanation can implement the present invention adequately. Examples are given below for the sake of further explanation. Therefore, the present invention is not limited to these examples. Furthermore, the nucleotide sequences in this specification are described in the direction from 5' to 3' unless stated otherwise.

EXAMPLES

Example 1

Construction of a Plasmid 1-a) Inositol Monophosphatase Expression Cassette

E. coli W3110 (NBRC 12713) was shake-cultured at 37° C. in LB medium (2 mL). After culture had been completed, the cells were collected from the culture broth, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. for 10 sec, 55° C. for 5 sec, 72° C. for 20 sec; 28 cycles) was carried out by the following primers, and the coding region of the suhB gene (SEQ ID NO: 3) was cloned.

[Chemical Formula 3]
Forward:
(SEQ ID NO: 9)
atgcatccgatgctgaac

Reverse:
(SEQ ID NO: 10)
ttaacgcttcagagcgtcg

The suhB coding region obtained was inserted transcribably downstream of a promoter of the following sequence.

[Chemical Formula 4]
Promoter:
(SEQ ID NO: 11)
gtcgtttttctgcttaggattttgttatttaaattaagcc tgtaatgccttgcttccattgcggataaatcctacttttt tattgccttcaaataaatttaaggagttc Specifically, a terminator sequence and the above promoter sequence were inserted at the multicloning site of plasmid pNFP-A51 (deposited as FERM P-22182 on Oct. 25, 2011 at the Incorporated Administrative Agency National Institute of Technology and Evaluation, Patent Microorganisms Depositary. International accession number: FERM BP-11515). The suhB coding region cloned as described above was ligated downstream of the promoter sequence introduced, and pNFP-A54 was constructed. The pNFP-A54 constructed was transfected into E. coli AKC-016 (deposited as FERM P-22014 on Apr. 20, 2011 at the Incorporated Administrative Agency National Institute of Technology and Evaluation, Patent Microorganisms Depositary. International accession number: FERM BP-11512) by the calcium chloride method (refer to Genetic Engineering Laboratory Notebook (vol. I), by Takaaki Tamura, Yodosha). High expression of inositol monophosphatase was confirmed in the soluble fraction of this E. coli by SDS-PAGE.

1-b) Inositol-1-Phosphate Synthase Expression Cassette

The cells were collected from the culture broth of distillery yeast, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. for 10 sec, 55° C. for 5 sec, 72° C. for 20 sec; 28 cycles) was carried out by the following primers, and the coding region of the INO1 gene (SEQ ID NO: 1) was cloned.

[Chemical Formula 5]
Forward:
(SEQ ID NO: 12)
atgacagaagataatattgctc

Reverse:
(SEQ ID NO: 13)
ttacaacaatctctcttcg

The ino1 coding region obtained was inserted transcribably downstream of a promoter of the following sequence.

[Chemical Formula 6]
Promoter:
(SEQ ID NO: 14)
ctcaagcccaaaggaagagtgaggcgagtcagtcgcgtaa tgcttaggcacaggattgatttgtcgcaatgattgacacg attccgcttgacgctgcgtaaggtttttgtaattttacag gcaaccttttattcactaacaaatagctggtggaa Specifically, a terminator sequence and the above promoter sequence were inserted at the multicloning site of the above plasmid pNFP-A51. The ino1 coding region cloned as described above was ligated downstream of the promoter sequence introduced, and pNFP-D78 was constructed. The pNFP-D78 constructed was transfected into E. coli AKC-016 (deposited as FERM P-22104 on Apr. 20, 2011 at the Incorporated Administrative Agency National Institute of Technology and Evaluation, Patent Microorganisms Depositary. International accession number: FERM BP-11512) by the calcium chloride method (refer to Genetic Engineering Laboratory Notebook (part I), by Takaaki Tamura, Yodosha). High expression of inositol-1-phosphate synthase was confirmed in the soluble fraction of this E. coli by SDS-PAGE.

1-c) Myo-Inositol Oxygenase Expression Cassette

DNA having a nucleotide sequence of SEQ ID NO: 5 was produced by artificial synthesis. Using this DNA as a template, PCR amplification (PrimeSTAR Max DNA Polymerase (product name, manufactured by Takara Bio), reaction conditions: 98° C. for 10 sec, 55° C. for 5 sec, 72° C. for 20 sec; 28 cycles) was carried out by the following primers, and a myo-inositol oxygenase (miox) gene was obtained.

[Chemical Formula 7]
Forward:
(SEQ ID NO: 15)
atgaaagttgatgttggtcctg (SEQ ID NO: 16)
Reverse:
ttaccaggacagggtgcc The miox coding region obtained was inserted transcribably downstream of a promoter of SEQ ID NO: 11. Specifically, a terminator sequence and the above promoter sequence were inserted at the multicloning site of the above plasmid pNFP-A51. The miox coding region cloned as described above was ligated downstream of the promoter sequence introduced, and pNFP-H26 was constructed. The pNFP-H26 constructed was transfected into E. coli FERM P-22104 by the calcium chloride method (refer to Genetic Engineering Laboratory Notebook (part I), by Takaaki Tamura, Yodosha). High expression of myo-inositol oxygenase was confirmed in the soluble fraction of this E. coli by SDS-PAGE.

1-d) Uronic Acid Dehydrogenase Expression Cassette

DNA having a nucleotide sequence of SEQ ID NO: 7 was produced by artificial synthesis. Using this DNA as a template, PCR amplification (PrimeSTAR Max DNA Polymerase (product name, manufactured by Takara Bio), reaction conditions: 98° C. for 10 sec, 55° C. for 5 sec, 72° C. for 20 sec; 28 cycles) was carried out by the following primers, and a uronic acid dehydrogenase (udh) gene was obtained.

[Chemical Formula 8]
Forward:
(SEQ ID NO: 17)
atgaccactaccccttcaat (SEQ ID NO: 18)
Reverse:
tcagttgaacgggccgg The udh coding region obtained was inserted transcribably downstream of a promoter of SEQ ID NO: 11. Specifically, a terminator sequence and the above promoter sequence were inserted at the multicloning site of the above plasmid pNFP-A51. The udh coding region cloned as described above was ligated downstream of the promoter sequence introduced, and pNFP-H45 was constructed. The pNFP-H45 constructed was transfected into E. coli FERM P-22104 by the calcium chloride method (refer to Genetic Engineering Laboratory Notebook (part I), by Takaaki Tamura, Yodosha). High expression of uronic acid dehydrogenase was confirmed in the soluble fraction of this E. coli by SDS-PAGE.

1-e) Construction of a Plasmid for Transformation p-NFP-D78 produced as described above was digested by Sal I, blunted, and the 5' end dephosphorylated. The suhB expression cassette was cloned in pNFP-A54, and ligated into pNFP-D78. pNFP-G22 having an INO1 expression cassette and an suhB expression cassette in the forward direction ligated in pNFP-D78 was obtained. Next, p-NFP-G22 was digested by Sal I, blunted, and the 5' end dephosphorylated. The miox expression cassette in pNFP-H26 and the udh expression cassette in pNFP-H45 produced in Example 1 were cloned, and the two expression cassettes were ligated into pNFP-G22. A plasmid of the present invention having a miox expression cassette and a udh expression cassette in the forward direction ligated in pNFP-G22 was obtained.

Example 2

2-a) Glucaric Acid Production by Transformants Transfected by an Expression Cassette-Containing Plasmid Using a Jar Fermenter A plasmid of the present invention constructed according to the above procedure was transfected into E. coli AKC-016 (deposited as FERM P-22014 on Apr. 20, 2011 at the Incorporated Administrative Agency National Institute of Technology and Evaluation, Patent Microorganisms Depositary. International accession number: FERM BP-11512) by the calcium chloride method (refer to Genetic Engineering Laboratory Notebook (part I), by Takaaki Tamura, Yodosha).

The transformant obtained was cultured for one day at 37° C. on LB plates containing ampicillin (100 mg/L) to form colonies. Thirty milliliters of LB medium containing ampicillin (100 mg/L) was placed in a 150 mL flask and inoculated by a platinum loop with colonies from the above plate. Culture was carried out at 37° C. for 3-5 hours at 180 rpm until OD (600 nm) reached approximately 0.5. This was taken as preculture broth for the main culture.

A quantity of 10 g/L of glucose and 300 mL of synthetic medium (Table 1) containing 100 mg/L of ampicillin were placed in a 1000 mL jar fermenter; 6 mL of preculture broth was added, and the main culture (glucaric acid production test using a jar fermenter) was conducted. The culture conditions were as follows: Culture temperature 32° C.; culture pH 6.0 [lower limit]; alkali added 28% (W/V) ammonia water; stirring 850 rpm; ventilation 1 vvm. The glucose feed solution (Table 2) that served as the raw material was added as was appropriate to make a glucose concentration of 0-5 g/L in the culture broth.

[Table 1]

TABLE 1

| Synthetic medium composition | |
|---|---|
| KH$_2$PO$_4$ | 13.3 g |
| (NH$_4$)$_2$HPO$_4$ | 4 g |
| MgSO$_4$•7H$_2$O | 1.2 g |
| EDTA•2Na | 8.4 mg |
| CoCl$_2$•6H$_2$O | 2.5 mg |
| MnCl$_2$•4H$_2$O | 15 mg |
| CuCl$_2$•2H$_2$O | 1.5 mg |
| H$_3$BO$_3$ | 3 mg |
| Na$_2$MoO$_4$•2H$_2$O | 2.5 mg |
| Zn(CH$_3$COO)$_2$•2H$_2$O | 13 mg |
| FeCl$_3$•6H$_2$O | 100 mg |
| total | 1 L |

Adjusted to pH 6.3 using 8N KOH.

[Table 2]

TABLE 2

| Glucose feed solution | |
|---|---|
| Glucose | 700 g |
| MgSO$_4$•7H$_2$0 | 20 g |
| EDTA•2Na | 13 mg |
| CoCl$_2$•6H$_2$0 | 5 mg |
| MnCl$_2$•4H$_2$0 | 29 mg |
| CuCl$_2$•2H$_2$0 | 4 mg |
| H$_3$BO$_3$ | 5 mg |
| Na$_2$Mo0$_4$•2H$_2$0 | 4 mg |
| Zn(CH$_3$C00)$_2$•2H$_2$0 | 21 mg |
| FeCl$_3$•6H$_2$0 | 41 mg |
| total | 1 L |

The above culture broth was centrifuged at 4° C. for 10 min at 10,000×g, and the supernatant was collected. The glucaric acid concentration in the culture supernatant was assayed by HPLC (detector: RI, column temperature: 40° C., flow rate: 1 mL/min, mobile phase 0.1% formic acid) by linking a Shim-Pak SCR-H (guard column) and Shim-Pak SCR-101H (both trade names, manufactured by Shimadzu GLC, Ltd.).

As a result, approximately 73 g/L (culture time 68 hours) of glucaric acid was produced in the culture supernatant of this transformant by enhancing the inositol monophosphatase activity in a transformant possessing an inositol-1-phosphate synthase gene, inositol monophosphatase gene, myo-inositol oxygenase gene, and uronic acid dehydrogenase gene according to the present invention.

Reference Example

Only 0.26 g/L of glucaric acid was produced with a culture time of 68 hours when a glucaric acid production test was conducted in accordance with Example 2 except that a transformant that does not overproduce inositol monophosphatase was produced and this unenhanced inositol monophosphatase strain was used.

When it is stated that the plasmids and microorganisms mentioned in this specification have been deposited, all were deposited with the (name of depository institution) "IPOD National Institute of Technology and Evaluation, Patent Microorganisms Depositary (IPOD, NITE)"; (address of depository institution) Central 6, 1-1-1 Higashi, Tsukuba-shi, Ibaraki-ken, 305-8566, JAPAN."

INDUSTRIAL APPLICABILITY

The present invention can be utilized in the industrial fermentative production of glucaric acid.

The invention claimed is:

1. A method of producing glucaric acid comprising:

(1) providing a *Escherichia coli* strain transformed with an overexpression vector comprising a gene encoding inositol monophosphatase, and having genes encoding inositol-1-phospahte synthase, myo-inositol oxygenase, and uronate dehydrogenase;

(2) growing and/or maintaining the transformed *Escherichia coli* strain with a carbon source under conditions suitable to convert the carbon source to glucaric acid and/or glucarate; and (3) separating the glucaric acid or glucarate from the transformed *Escherichia coli* strain.

2. The method according to claim 1, wherein the carbon source contains a compound that can be converted into glucose-6-phosphate within the transformed *Escherichia coli* strain.

3. The method according to claim 2, wherein the carbon source is one or more selected from the group consisting of D-glucose, sucrose, oligosaccharide, polysaccharide, starch, cellulose, rice bran, molasses, and biomass containing D-glucose.

* * * * *

SEQUENCE LISTING

```
<160> NUMBER OF SEQ ID NOS: 18

<210> SEQ ID NO 1
<211> LENGTH: 1602
<212> TYPE: DNA
<213> ORGANISM: Saccharomyces cerevisiae
<220> FEATURE:
<221> NAME/KEY: CDS
<222> LOCATION: (1)..(1602)

<400> SEQUENCE: 1 atg aca gaa gat aat att gct cca atc acc tcc gtt aaa gta gtt acc      48
Met Thr Glu Asp Asn Ile Ala Pro Ile Thr Ser Val Lys Val Val Thr
1               5                   10                  15 gac aag tgc acg tac aag gac aac gag ctg ctc acc aag tac agc tac      96
Asp Lys Cys Thr Tyr Lys Asp Asn Glu Leu Leu Thr Lys Tyr Ser Tyr
                20                  25                  30 gaa aat gct gta gtt acg aag aca gct agt ggc cgc ttc gat gtc acg     144
Glu Asn Ala Val Val Thr Lys Thr Ala Ser Gly Arg Phe Asp Val Thr
            35                  40                  45 ccc act gtt caa gac tac gtg ttc aaa ctt gac tta aaa aag ccg gaa     192
Pro Thr Val Gln Asp Tyr Val Phe Lys Leu Asp Leu Lys Lys Pro Glu
        50                  55                  60 aaa cta gga att atg ctc att ggg tta ggt ggc aac aat ggc tcc acc     240
Lys Leu Gly Ile Met Leu Ile Gly Leu Gly Gly Asn Asn Gly Ser Thr
65                  70                  75                  80
```

```
tta gtg gcc tcg gta ttg gcg aat aag cac aat gtg gag ttt caa act      288
Leu Val Ala Ser Val Leu Ala Asn Lys His Asn Val Glu Phe Gln Thr
                85                  90                  95 aag gaa ggc gtt aag caa cca aac tac ttc ggc tcc atg act caa tgt      336
Lys Glu Gly Val Lys Gln Pro Asn Tyr Phe Gly Ser Met Thr Gln Cys
            100                 105                 110 tct acc ttg aaa ctg ggt gtc gat gcg gag ggg aat gac gtt tat gct      384
Ser Thr Leu Lys Leu Gly Val Asp Ala Glu Gly Asn Asp Val Tyr Ala
        115                 120                 125 cct ttt aac tct ctg ttg ccc atg gtt agc cca aac gac ttt gtc gtc      432
Pro Phe Asn Ser Leu Leu Pro Met Val Ser Pro Asn Asp Phe Val Val
    130                 135                 140 tct ggt tgg gac atc aat aac gca gat cta tac gaa gct atg cag aga      480
Ser Gly Trp Asp Ile Asn Asn Ala Asp Leu Tyr Glu Ala Met Gln Arg
145                 150                 155                 160 agt cag gtt ctc gaa tat gat ctg caa caa cgc ttg aag gcg aag atg      528
Ser Gln Val Leu Glu Tyr Asp Leu Gln Gln Arg Leu Lys Ala Lys Met
                165                 170                 175 tcc ttg gtg aag cct ctt cct tcc att tac tac cct gat ttc att gca      576
Ser Leu Val Lys Pro Leu Pro Ser Ile Tyr Tyr Pro Asp Phe Ile Ala
            180                 185                 190 gct aat caa gat gag aga gcc aat aac tgc atc aat ttg gat gaa aaa      624
Ala Asn Gln Asp Glu Arg Ala Asn Asn Cys Ile Asn Leu Asp Glu Lys
        195                 200                 205 ggc aac gta acc acg agg ggt aag tgg gcc cat ctg caa cgc atc aga      672
Gly Asn Val Thr Thr Arg Gly Lys Trp Ala His Leu Gln Arg Ile Arg
    210                 215                 220 cgc gat att cag aat ttc aaa gaa gaa aac gcc ctt gat aaa gta atc      720
Arg Asp Ile Gln Asn Phe Lys Glu Glu Asn Ala Leu Asp Lys Val Ile
225                 230                 235                 240 gtt ctt tgg act gca aat act gag agg tca gta gaa gta tct cct ggt      768
Val Leu Trp Thr Ala Asn Thr Glu Arg Ser Val Glu Val Ser Pro Gly
                245                 250                 255 gtt aat gac acc atg gaa aac ctc ttg cag tct att aag aat gac cat      816
Val Asn Asp Thr Met Glu Asn Leu Leu Gln Ser Ile Lys Asn Asp His
            260                 265                 270 gaa gag att gct cct tcc acg atc ttt gca gca gca tct atc ttg gaa      864
Glu Glu Ile Ala Pro Ser Thr Ile Phe Ala Ala Ala Ser Ile Leu Glu
        275                 280                 285 ggt gtc ccc tat att aat ggt tca ccg cag aat act ttt gtt ccc ggc      912
Gly Val Pro Tyr Ile Asn Gly Ser Pro Gln Asn Thr Phe Val Pro Gly
    290                 295                 300 ttg gtt cag ctg gct gag cat gag ggt aca ttc att gcg gga gac gat      960
Leu Val Gln Leu Ala Glu His Glu Gly Thr Phe Ile Ala Gly Asp Asp
305                 310                 315                 320 ctc aag tcg gga caa acc aag ttg aag tct gtt ctg gcc cag ttc tta     1008
Leu Lys Ser Gly Gln Thr Lys Leu Lys Ser Val Leu Ala Gln Phe Leu
                325                 330                 335 gtg gat gca ggt att aaa ccg gtc tcc att gca tcc tat aac cat tta     1056
Val Asp Ala Gly Ile Lys Pro Val Ser Ile Ala Ser Tyr Asn His Leu
            340                 345                 350 ggc aat aat gac ggt tat aac tta tct gct cca aaa caa ttt agg tct     1104
Gly Asn Asn Asp Gly Tyr Asn Leu Ser Ala Pro Lys Gln Phe Arg Ser
        355                 360                 365 aag gag att tcc aaa agt tct gtc ata gat gac atc atc gcg tct aat     1152
Lys Glu Ile Ser Lys Ser Ser Val Ile Asp Asp Ile Ile Ala Ser Asn
    370                 375                 380 gat atc ttg tac aat gat aaa ctg ggt aaa aaa gtt gac cac tgc att     1200
Asp Ile Leu Tyr Asn Asp Lys Leu Gly Lys Lys Val Asp His Cys Ile
```

```
                385                 390                 395                 400
gtc att aaa tat atg aag ccc gtc ggg gac tca aaa gtg gca atg gac     1248
Val Ile Lys Tyr Met Lys Pro Val Gly Asp Ser Lys Val Ala Met Asp
                    405                 410                 415 gag tat tac agt gag ttg atg tta ggt ggc cat aac cgg att tcc att     1296
Glu Tyr Tyr Ser Glu Leu Met Leu Gly Gly His Asn Arg Ile Ser Ile
                420                 425                 430 cac aat gtt tgc gaa gat tct tta ctg gct acg ccc ttg atc atc gat     1344
His Asn Val Cys Glu Asp Ser Leu Leu Ala Thr Pro Leu Ile Ile Asp
            435                 440                 445 ctt tta gtc atg act gag ttt tgt aca aga gtg tcc tat aag aag gtg     1392
Leu Leu Val Met Thr Glu Phe Cys Thr Arg Val Ser Tyr Lys Lys Val
        450                 455                 460 gac cca gtt aaa gaa gat gct ggc aaa ttt gag aac ttt tat cca gtt     1440
Asp Pro Val Lys Glu Asp Ala Gly Lys Phe Glu Asn Phe Tyr Pro Val
465                 470                 475                 480 tta acc ttc ttg agt tac tgg tta aaa gct cca tta aca aga cca gga     1488
Leu Thr Phe Leu Ser Tyr Trp Leu Lys Ala Pro Leu Thr Arg Pro Gly
                    485                 490                 495 ttt cac ccg gtg aat ggc tta aac aag caa aga acc gcc tta gaa aat     1536
Phe His Pro Val Asn Gly Leu Asn Lys Gln Arg Thr Ala Leu Glu Asn
                500                 505                 510 ttt tta aga ttg ttg att gga ttg cct tct caa aac gaa cta aga ttc     1584
Phe Leu Arg Leu Leu Ile Gly Leu Pro Ser Gln Asn Glu Leu Arg Phe
            515                 520                 525 gaa gag aga ttg ttg taa                                              1602
Glu Glu Arg Leu Leu
        530

<210> SEQ ID NO 2
<211> LENGTH: 533
<212> TYPE: PRT
<213> ORGANISM: Saccharomyces cerevisiae

<400> SEQUENCE: 2

Met Thr Glu Asp Asn Ile Ala Pro Ile Thr Ser Val Lys Val Val Thr
1               5                   10                  15

Asp Lys Cys Thr Tyr Lys Asp Asn Glu Leu Leu Thr Lys Tyr Ser Tyr
                20                  25                  30

Glu Asn Ala Val Val Thr Lys Thr Ala Ser Gly Arg Phe Asp Val Thr
            35                  40                  45

Pro Thr Val Gln Asp Tyr Val Phe Lys Leu Asp Leu Lys Lys Pro Glu
        50                  55                  60

Lys Leu Gly Ile Met Leu Ile Gly Leu Gly Asn Asn Gly Ser Thr
65                  70                  75                  80

Leu Val Ala Ser Val Leu Ala Asn Lys His Asn Val Glu Phe Gln Thr
                85                  90                  95

Lys Glu Gly Val Lys Gln Pro Asn Tyr Phe Gly Ser Met Thr Gln Cys
            100                 105                 110

Ser Thr Leu Lys Leu Gly Val Asp Ala Glu Gly Asn Asp Val Tyr Ala
        115                 120                 125

Pro Phe Asn Ser Leu Leu Pro Met Val Ser Pro Asn Asp Phe Val Val
    130                 135                 140

Ser Gly Trp Asp Ile Asn Asn Ala Asp Leu Tyr Glu Ala Met Gln Arg
145                 150                 155                 160

Ser Gln Val Leu Glu Tyr Asp Leu Gln Gln Arg Leu Lys Ala Lys Met
                165                 170                 175
```

Ser Leu Val Lys Pro Leu Pro Ser Ile Tyr Tyr Pro Asp Phe Ile Ala
            180                 185                 190

Ala Asn Gln Asp Glu Arg Ala Asn Asn Cys Ile Asn Leu Asp Glu Lys
        195                 200                 205

Gly Asn Val Thr Thr Arg Gly Lys Trp Ala His Leu Gln Arg Ile Arg
    210                 215                 220

Arg Asp Ile Gln Asn Phe Lys Glu Glu Asn Ala Leu Asp Lys Val Ile
225                 230                 235                 240

Val Leu Trp Thr Ala Asn Thr Glu Arg Ser Val Glu Val Ser Pro Gly
                245                 250                 255

Val Asn Asp Thr Met Glu Asn Leu Leu Gln Ser Ile Lys Asn Asp His
            260                 265                 270

Glu Glu Ile Ala Pro Ser Thr Ile Phe Ala Ala Ala Ser Ile Leu Glu
        275                 280                 285

Gly Val Pro Tyr Ile Asn Gly Ser Pro Gln Asn Thr Phe Val Pro Gly
    290                 295                 300

Leu Val Gln Leu Ala Glu His Glu Gly Thr Phe Ile Ala Gly Asp Asp
305                 310                 315                 320

Leu Lys Ser Gly Gln Thr Lys Leu Lys Ser Val Leu Ala Gln Phe Leu
                325                 330                 335

Val Asp Ala Gly Ile Lys Pro Val Ser Ile Ala Ser Tyr Asn His Leu
            340                 345                 350

Gly Asn Asn Asp Gly Tyr Asn Leu Ser Ala Pro Lys Gln Phe Arg Ser
        355                 360                 365

Lys Glu Ile Ser Lys Ser Ser Val Ile Asp Asp Ile Ile Ala Ser Asn
    370                 375                 380

Asp Ile Leu Tyr Asn Asp Lys Leu Gly Lys Lys Val Asp His Cys Ile
385                 390                 395                 400

Val Ile Lys Tyr Met Lys Pro Val Gly Asp Ser Lys Val Ala Met Asp
                405                 410                 415

Glu Tyr Tyr Ser Glu Leu Met Leu Gly Gly His Asn Arg Ile Ser Ile
            420                 425                 430

His Asn Val Cys Glu Asp Ser Leu Leu Ala Thr Pro Leu Ile Ile Asp
        435                 440                 445

Leu Leu Val Met Thr Glu Phe Cys Thr Arg Val Ser Tyr Lys Lys Val
    450                 455                 460

Asp Pro Val Lys Glu Asp Ala Gly Lys Phe Glu Asn Phe Tyr Pro Val
465                 470                 475                 480

Leu Thr Phe Leu Ser Tyr Trp Leu Lys Ala Pro Leu Thr Arg Pro Gly
                485                 490                 495

Phe His Pro Val Asn Gly Leu Asn Lys Gln Arg Thr Ala Leu Glu Asn
            500                 505                 510

Phe Leu Arg Leu Leu Ile Gly Leu Pro Ser Gln Asn Glu Leu Arg Phe
        515                 520                 525

Glu Glu Arg Leu Leu
    530

<210> SEQ ID NO 3
<211> LENGTH: 804
<212> TYPE: DNA
<213> ORGANISM: Escherichia coli
<220> FEATURE:
<221> NAME/KEY: CDS
<222> LOCATION: (1)..(804)

<400> SEQUENCE: 3

```
atg cat ccg atg ctg aac atc gcc gtg cgc gca gcg cgc aag gcg ggt        48
Met His Pro Met Leu Asn Ile Ala Val Arg Ala Ala Arg Lys Ala Gly
1               5                   10                  15 aat tta att gcc aaa aac tat gaa acc ccg gac gct gta gaa gcg agc        96
Asn Leu Ile Ala Lys Asn Tyr Glu Thr Pro Asp Ala Val Glu Ala Ser
            20                  25                  30 cag aaa ggc agt aac gat ttc gtg acc aac gta gat aaa gct gcc gaa       144
Gln Lys Gly Ser Asn Asp Phe Val Thr Asn Val Asp Lys Ala Ala Glu
        35                  40                  45 gcg gtg att atc gac acg att cgt aaa tct tac cca cag cac acc atc       192
Ala Val Ile Ile Asp Thr Ile Arg Lys Ser Tyr Pro Gln His Thr Ile
    50                  55                  60 atc acc gaa gaa agc ggt gaa ctt gaa ggt act gat cag gat gtt caa       240
Ile Thr Glu Glu Ser Gly Glu Leu Glu Gly Thr Asp Gln Asp Val Gln
65                  70                  75                  80 tgg gtt atc gat cca ctg gat ggc act acc aac ttt atc aaa cgt ctg       288
Trp Val Ile Asp Pro Leu Asp Gly Thr Thr Asn Phe Ile Lys Arg Leu
                85                  90                  95 ccg cac ttc gcg gta tct atc gct gtt cgt atc aaa ggc cgc acc gaa       336
Pro His Phe Ala Val Ser Ile Ala Val Arg Ile Lys Gly Arg Thr Glu
            100                 105                 110 gtt gct gtg gta tac gat cct atg cgt aac gaa ctg ttc acc gcc act       384
Val Ala Val Val Tyr Asp Pro Met Arg Asn Glu Leu Phe Thr Ala Thr
        115                 120                 125 cgc ggt cag ggc gca cag ctg aac ggc tac cga ctg cgc ggc agc acc       432
Arg Gly Gln Gly Ala Gln Leu Asn Gly Tyr Arg Leu Arg Gly Ser Thr
    130                 135                 140 gct cgc gat ctc gac ggt act att ctg gcg acc ggc ttc ccg ttc aaa       480
Ala Arg Asp Leu Asp Gly Thr Ile Leu Ala Thr Gly Phe Pro Phe Lys
145                 150                 155                 160 gca aaa cag tac gcc act acc tac atc aac atc gtc ggc aaa ctg ttc       528
Ala Lys Gln Tyr Ala Thr Thr Tyr Ile Asn Ile Val Gly Lys Leu Phe
                165                 170                 175 aac gaa tgt gca gac ttc cgt cgt acc ggt tct gcg gcg ctg gat ctg       576
Asn Glu Cys Ala Asp Phe Arg Arg Thr Gly Ser Ala Ala Leu Asp Leu
            180                 185                 190 gct tac gtc gct gcg ggt cgt gtt gac ggt ttc ttt gaa atc ggt ctg       624
Ala Tyr Val Ala Ala Gly Arg Val Asp Gly Phe Phe Glu Ile Gly Leu
        195                 200                 205 cgc ccg tgg gac ttc gcc gca ggc gag ctg ctg gtt cgt gaa gcg ggc       672
Arg Pro Trp Asp Phe Ala Ala Gly Glu Leu Leu Val Arg Glu Ala Gly
    210                 215                 220 ggc atc gtc agc gac ttc acc ggt ggt cat aac tac atg ctg acc ggt       720
Gly Ile Val Ser Asp Phe Thr Gly Gly His Asn Tyr Met Leu Thr Gly
225                 230                 235                 240 aac atc gtt gct ggt aac ccg cgc gtt gtt aaa gcc atg ctg gcg aac       768
Asn Ile Val Ala Gly Asn Pro Arg Val Val Lys Ala Met Leu Ala Asn
                245                 250                 255 atg cgt gac gag tta agc gac gct ctg aag cgt taa                       804
Met Arg Asp Glu Leu Ser Asp Ala Leu Lys Arg
            260                 265
```

<210> SEQ ID NO 4
<211> LENGTH: 267
<212> TYPE: PRT
<213> ORGANISM: Escherichia coli

<400> SEQUENCE: 4

```
Met His Pro Met Leu Asn Ile Ala Val Arg Ala Ala Arg Lys Ala Gly
1               5                   10                  15
```

```
Asn Leu Ile Ala Lys Asn Tyr Glu Thr Pro Asp Ala Val Glu Ala Ser
             20                  25                  30

Gln Lys Gly Ser Asn Asp Phe Val Thr Asn Val Asp Lys Ala Ala Glu
         35                  40                  45

Ala Val Ile Ile Asp Thr Ile Arg Lys Ser Tyr Pro Gln His Thr Ile
     50                  55                  60

Ile Thr Glu Glu Ser Gly Glu Leu Glu Gly Thr Asp Gln Asp Val Gln
 65                  70                  75                  80

Trp Val Ile Asp Pro Leu Asp Gly Thr Thr Asn Phe Ile Lys Arg Leu
                 85                  90                  95

Pro His Phe Ala Val Ser Ile Ala Val Arg Ile Lys Gly Arg Thr Glu
            100                 105                 110

Val Ala Val Val Tyr Asp Pro Met Arg Asn Glu Leu Phe Thr Ala Thr
        115                 120                 125

Arg Gly Gln Gly Ala Gln Leu Asn Gly Tyr Arg Leu Arg Gly Ser Thr
    130                 135                 140

Ala Arg Asp Leu Asp Gly Thr Ile Leu Ala Thr Gly Phe Pro Phe Lys
145                 150                 155                 160

Ala Lys Gln Tyr Ala Thr Thr Tyr Ile Asn Ile Val Gly Lys Leu Phe
                165                 170                 175

Asn Glu Cys Ala Asp Phe Arg Arg Thr Gly Ser Ala Ala Leu Asp Leu
            180                 185                 190

Ala Tyr Val Ala Ala Gly Arg Val Asp Gly Phe Phe Glu Ile Gly Leu
        195                 200                 205

Arg Pro Trp Asp Phe Ala Ala Gly Glu Leu Leu Val Arg Glu Ala Gly
    210                 215                 220

Gly Ile Val Ser Asp Phe Thr Gly Gly His Asn Tyr Met Leu Thr Gly
225                 230                 235                 240

Asn Ile Val Ala Gly Asn Pro Arg Val Val Lys Ala Met Leu Ala Asn
                245                 250                 255

Met Arg Asp Glu Leu Ser Asp Ala Leu Lys Arg
            260                 265

<210> SEQ ID NO 5
<211> LENGTH: 858
<212> TYPE: DNA
<213> ORGANISM: Artificial Sequence
<220> FEATURE:
<223> OTHER INFORMATION: miox gene coding region
<220> FEATURE:
<221> NAME/KEY: CDS
<222> LOCATION: (1)..(858)

<400> SEQUENCE: 5 atg aaa gtt gat gtt ggt cct gat ccg tct ctg gtt tat cgt cca gac      48
Met Lys Val Asp Val Gly Pro Asp Pro Ser Leu Val Tyr Arg Pro Asp
 1               5                  10                  15 gtg gat ccg gag atg gca aag agc aaa gac tct ttc cgt aac tac act      96
Val Asp Pro Glu Met Ala Lys Ser Lys Asp Ser Phe Arg Asn Tyr Thr
             20                  25                  30 tct ggt ccg ctg ctg gat cgc gtt ttc acg acc tac aaa ctg atg cac     144
Ser Gly Pro Leu Leu Asp Arg Val Phe Thr Thr Tyr Lys Leu Met His
         35                  40                  45 acc cat cag acc gtt gat ttc gtg agc cgc aag cgc atc cag tat ggt     192
Thr His Gln Thr Val Asp Phe Val Ser Arg Lys Arg Ile Gln Tyr Gly
     50                  55                  60 tct ttc tct tac aaa aag atg acc att atg gag gct gtt ggt atg ctg     240
```

```
Ser Phe Ser Tyr Lys Lys Met Thr Ile Met Glu Ala Val Gly Met Leu
 65                  70                  75                  80 gat gac ctg gtt gac gaa agc gac cct gac gtt gac ttc cct aac tct      288
Asp Asp Leu Val Asp Glu Ser Asp Pro Asp Val Asp Phe Pro Asn Ser
                     85                  90                  95 ttc cat gca ttt cag acc gcc gaa ggt att cgt aaa gct cat cct gat      336
Phe His Ala Phe Gln Thr Ala Glu Gly Ile Arg Lys Ala His Pro Asp
            100                 105                 110 aaa gat tgg ttc cac ctg gtc ggt ctg ctg cac gac ctg ggt aag atc      384
Lys Asp Trp Phe His Leu Val Gly Leu Leu His Asp Leu Gly Lys Ile
        115                 120                 125 atg gcg ctg tgg ggc gaa cca caa tgg gcg gta gtg ggc gat act ttc      432
Met Ala Leu Trp Gly Glu Pro Gln Trp Ala Val Val Gly Asp Thr Phe
    130                 135                 140 ccg gtg ggc tgc cgc cca cag gca tcc gtg gtc ttc tgc gac tct acc      480
Pro Val Gly Cys Arg Pro Gln Ala Ser Val Val Phe Cys Asp Ser Thr
145                 150                 155                 160 ttc cag gat aac ccg gat ctg cag gat ccg cgc tat tcc acc gaa ctg      528
Phe Gln Asp Asn Pro Asp Leu Gln Asp Pro Arg Tyr Ser Thr Glu Leu
                165                 170                 175 ggc atg tac cag ccg cat tgc ggc ctg gag aac gtt ctg atg tct tgg      576
Gly Met Tyr Gln Pro His Cys Gly Leu Glu Asn Val Leu Met Ser Trp
            180                 185                 190 ggt cac gac gag tac ctg tat cag atg atg aaa ttc aac aaa ttc tcc      624
Gly His Asp Glu Tyr Leu Tyr Gln Met Met Lys Phe Asn Lys Phe Ser
        195                 200                 205 ctg ccg tcc gag gca ttt tac atg atc cgt ttt cac tcc ttc tac ccg      672
Leu Pro Ser Glu Ala Phe Tyr Met Ile Arg Phe His Ser Phe Tyr Pro
    210                 215                 220 tgg cat acc ggt ggc gat tat cgt cag ctg tgc tct cag cag gat ctg      720
Trp His Thr Gly Gly Asp Tyr Arg Gln Leu Cys Ser Gln Gln Asp Leu
225                 230                 235                 240 gat atg ctg ccg tgg gtt cag gag ttc aat aaa ttc gac ctg tat acc      768
Asp Met Leu Pro Trp Val Gln Glu Phe Asn Lys Phe Asp Leu Tyr Thr
                245                 250                 255 aaa tgc cct gac ctg cca gat gtt gaa tcc ctg cgc cca tac tac caa      816
Lys Cys Pro Asp Leu Pro Asp Val Glu Ser Leu Arg Pro Tyr Tyr Gln
            260                 265                 270 ggc ctg att gac aaa tac tgc ccg ggc acc ctg tcc tgg taa              858
Gly Leu Ile Asp Lys Tyr Cys Pro Gly Thr Leu Ser Trp
        275                 280                 285
```

<210> SEQ ID NO 6
<211> LENGTH: 285
<212> TYPE: PRT
<213> ORGANISM: Artificial Sequence
<220> FEATURE:
<223> OTHER INFORMATION: Synthetic Construct

<400> SEQUENCE: 6

```
Met Lys Val Asp Val Gly Pro Asp Pro Ser Leu Val Tyr Arg Pro Asp
1               5                   10                  15

Val Asp Pro Glu Met Ala Lys Ser Lys Asp Ser Phe Arg Asn Tyr Thr
            20                  25                  30

Ser Gly Pro Leu Leu Asp Arg Val Phe Thr Thr Tyr Lys Leu Met His
        35                  40                  45

Thr His Gln Thr Val Asp Phe Val Ser Arg Lys Arg Ile Gln Tyr Gly
    50                  55                  60

Ser Phe Ser Tyr Lys Lys Met Thr Ile Met Glu Ala Val Gly Met Leu
65                  70                  75                  80
```

```
Asp Asp Leu Val Asp Glu Ser Asp Pro Asp Val Asp Phe Pro Asn Ser
                85                  90                  95

Phe His Ala Phe Gln Thr Ala Glu Gly Ile Arg Lys Ala His Pro Asp
            100                 105                 110

Lys Asp Trp Phe His Leu Val Gly Leu Leu His Asp Leu Gly Lys Ile
        115                 120                 125

Met Ala Leu Trp Gly Glu Pro Gln Trp Ala Val Val Gly Asp Thr Phe
    130                 135                 140

Pro Val Gly Cys Arg Pro Gln Ala Ser Val Val Phe Cys Asp Ser Thr
145                 150                 155                 160

Phe Gln Asp Asn Pro Asp Leu Gln Asp Pro Arg Tyr Ser Thr Glu Leu
                165                 170                 175

Gly Met Tyr Gln Pro His Cys Gly Leu Glu Asn Val Leu Met Ser Trp
            180                 185                 190

Gly His Asp Glu Tyr Leu Tyr Gln Met Met Lys Phe Asn Lys Phe Ser
        195                 200                 205

Leu Pro Ser Glu Ala Phe Tyr Met Ile Arg Phe His Ser Phe Tyr Pro
    210                 215                 220

Trp His Thr Gly Gly Asp Tyr Arg Gln Leu Cys Ser Gln Gln Asp Leu
225                 230                 235                 240

Asp Met Leu Pro Trp Val Gln Glu Phe Asn Lys Phe Asp Leu Tyr Thr
                245                 250                 255

Lys Cys Pro Asp Leu Pro Asp Val Glu Ser Leu Arg Pro Tyr Tyr Gln
            260                 265                 270

Gly Leu Ile Asp Lys Tyr Cys Pro Gly Thr Leu Ser Trp
        275                 280                 285

<210> SEQ ID NO 7
<211> LENGTH: 807
<212> TYPE: DNA
<213> ORGANISM: Artificial Sequence
<220> FEATURE:
<223> OTHER INFORMATION: udh gene coding region
<220> FEATURE:
<221> NAME/KEY: CDS
<222> LOCATION: (1)..(807)

<400> SEQUENCE: 7 atg acc act acc ccc ttc aat cgc ctg ctg ctc acc gga gcc gca ggc      48
Met Thr Thr Thr Pro Phe Asn Arg Leu Leu Leu Thr Gly Ala Ala Gly
1               5                   10                  15 ggc ctg ggc aag gtc ctt cgc gaa cgc ctg aaa ggc tac gcc gag gtc      96
Gly Leu Gly Lys Val Leu Arg Glu Arg Leu Lys Gly Tyr Ala Glu Val
            20                  25                  30 ctg cgc ctg tct gac atc agc ccc atg gcc ccg gcc gcg ggc ccg cat     144
Leu Arg Leu Ser Asp Ile Ser Pro Met Ala Pro Ala Ala Gly Pro His
        35                  40                  45 gaa gaa gtc att acc tgt gac ctg gcc gac aag gct gcg gtc cat acc     192
Glu Glu Val Ile Thr Cys Asp Leu Ala Asp Lys Ala Ala Val His Thr
    50                  55                  60 ctg gtc gag ggc gta gac gcc atc atc cac ttt ggc ggg gtt tct acc     240
Leu Val Glu Gly Val Asp Ala Ile Ile His Phe Gly Gly Val Ser Thr
65                  70                  75                  80 gaa cac gcc ttc gaa gag att ctc ggc ccc aat atc tgc ggc gtg ttc     288
Glu His Ala Phe Glu Glu Ile Leu Gly Pro Asn Ile Cys Gly Val Phe
                85                  90                  95 cac gtg tac gag gcg gcg cgc aag cac ggg gtc aag cgc atc atc ttc     336
His Val Tyr Glu Ala Ala Arg Lys His Gly Val Lys Arg Ile Ile Phe
```

```
gcc agc tcc aac cac acc atc ggt ttc tat cgc cag gat gag cgc atc      384
Ala Ser Ser Asn His Thr Ile Gly Phe Tyr Arg Gln Asp Glu Arg Ile
        115                 120                 125 gac gct cac gcg ccg cgc cgg ccc gac agc tat tac ggg ctg tcc aag      432
Asp Ala His Ala Pro Arg Arg Pro Asp Ser Tyr Tyr Gly Leu Ser Lys
130                 135                 140 tgc tac ggc gaa gat gtg gcc agc ttc tac ttt gac cgc tac ggc atc      480
Cys Tyr Gly Glu Asp Val Ala Ser Phe Tyr Phe Asp Arg Tyr Gly Ile
145                 150                 155                 160 gag acc gtc agc att cgc atc ggc tcg tcg ttc ccg cag cca cag aac      528
Glu Thr Val Ser Ile Arg Ile Gly Ser Ser Phe Pro Gln Pro Gln Asn
                165                 170                 175 ctg cgc atg ctc tgc acc tgg ctc agt tac gac gac ctg gtg cag ttg      576
Leu Arg Met Leu Cys Thr Trp Leu Ser Tyr Asp Asp Leu Val Gln Leu
            180                 185                 190 atc gaa cgc ggg ctg ttc acc ccc ggg gtt ggc cac acc atc gtc tac      624
Ile Glu Arg Gly Leu Phe Thr Pro Gly Val Gly His Thr Ile Val Tyr
        195                 200                 205 ggc gcc tcc gac aat cgc acc gtg tgg tgg gac aac cgc cat gcc gcg      672
Gly Ala Ser Asp Asn Arg Thr Val Trp Trp Asp Asn Arg His Ala Ala
210                 215                 220 cac ctg ggc tat gta ccc aag gac agc tcc gaa acc ttc cgc gca gcc      720
His Leu Gly Tyr Val Pro Lys Asp Ser Ser Glu Thr Phe Arg Ala Ala
225                 230                 235                 240 gtg gag gcc caa ccg gca ccc gcc gcc gat gac ccg agc atg gtc tac      768
Val Glu Ala Gln Pro Ala Pro Ala Ala Asp Asp Pro Ser Met Val Tyr
                245                 250                 255 cag ggc ggc gct ttc gcc gtg gcc ggc ccg ttc aac tga                  807
Gln Gly Gly Ala Phe Ala Val Ala Gly Pro Phe Asn
            260                 265

<210> SEQ ID NO 8
<211> LENGTH: 268
<212> TYPE: PRT
<213> ORGANISM: Artificial Sequence
<220> FEATURE:
<223> OTHER INFORMATION: Synthetic Construct

<400> SEQUENCE: 8

Met Thr Thr Thr Pro Phe Asn Arg Leu Leu Leu Thr Gly Ala Ala Gly
1               5                   10                  15

Gly Leu Gly Lys Val Leu Arg Glu Arg Leu Lys Gly Tyr Ala Glu Val
            20                  25                  30

Leu Arg Leu Ser Asp Ile Ser Pro Met Ala Pro Ala Ala Gly Pro His
        35                  40                  45

Glu Glu Val Ile Thr Cys Asp Leu Ala Asp Lys Ala Val His Thr
    50                  55                  60

Leu Val Glu Gly Val Asp Ala Ile Ile His Phe Gly Gly Val Ser Thr
65                  70                  75                  80

Glu His Ala Phe Glu Glu Ile Leu Gly Pro Asn Ile Cys Gly Val Phe
                85                  90                  95

His Val Tyr Glu Ala Ala Arg Lys His Gly Val Lys Arg Ile Ile Phe
            100                 105                 110

Ala Ser Ser Asn His Thr Ile Gly Phe Tyr Arg Gln Asp Glu Arg Ile
        115                 120                 125
```

Asp Ala His Ala Pro Arg Arg Pro Asp Ser Tyr Tyr Gly Leu Ser Lys
    130                 135                 140

Cys Tyr Gly Glu Asp Val Ala Ser Phe Tyr Phe Asp Arg Tyr Gly Ile
145                 150                 155                 160

Glu Thr Val Ser Ile Arg Ile Gly Ser Ser Phe Pro Gln Pro Gln Asn
                165                 170                 175

Leu Arg Met Leu Cys Thr Trp Leu Ser Tyr Asp Asp Leu Val Gln Leu
            180                 185                 190

Ile Glu Arg Gly Leu Phe Thr Pro Gly Val Gly His Thr Ile Val Tyr
        195                 200                 205

Gly Ala Ser Asp Asn Arg Thr Val Trp Trp Asp Asn Arg His Ala Ala
    210                 215                 220

His Leu Gly Tyr Val Pro Lys Asp Ser Ser Glu Thr Phe Arg Ala Ala
225                 230                 235                 240

Val Glu Ala Gln Pro Ala Pro Ala Ala Asp Asp Pro Ser Met Val Tyr
                245                 250                 255

Gln Gly Gly Ala Phe Ala Val Ala Gly Pro Phe Asn
            260                 265

<210> SEQ ID NO 9
<211> LENGTH: 18
<212> TYPE: DNA
<213> ORGANISM: Artificial Sequence
<220> FEATURE:
<223> OTHER INFORMATION: Forward PCR Primer for suhB Coding Region

<400> SEQUENCE: 9
atgcatccga tgctgaac                                           18

<210> SEQ ID NO 10
<211> LENGTH: 19
<212> TYPE: DNA
<213> ORGANISM: Artificial Sequence
<220> FEATURE:
<223> OTHER INFORMATION: Reverse PCR Primer for suhB Coding Region

<400> SEQUENCE: 10
ttaacgcttc agagcgtcg                                          19

<210> SEQ ID NO 11
<211> LENGTH: 109
<212> TYPE: DNA
<213> ORGANISM: Artificial Sequence
<220> FEATURE:
<223> OTHER INFORMATION: Promoter for suhB coding region

<400> SEQUENCE: 11 gtcgttttc tgcttaggat tttgttattt aaattaagcc tgtaatgcct tgcttccatt    60
gcggataaat cctactttt tattgccttc aaataaattt aaggagttc              109

<210> SEQ ID NO 12
<211> LENGTH: 22
<212> TYPE: DNA
<213> ORGANISM: Artificial Sequence
<220> FEATURE:
<223> OTHER INFORMATION: Forward PCR Primer for INO1 Coding Region

<400> SEQUENCE: 12
atgacagaag ataatattgc tc					22

<210> SEQ ID NO 13
<211> LENGTH: 19
<212> TYPE: DNA
<213> ORGANISM: Artificial Sequence
<220> FEATURE:
<223> OTHER INFORMATION: Reverse PCR Primer for INO1 Coding Region

<400> SEQUENCE: 13
ttacaacaat ctctcttcg					19

<210> SEQ ID NO 14
<211> LENGTH: 155
<212> TYPE: DNA
<213> ORGANISM: Artificial Sequence
<220> FEATURE:
<223> OTHER INFORMATION: Promoter for INO1 coding sequence

<400> SEQUENCE: 14
ctcaagccca aaggaagagt gaggcgagtc agtcgcgtaa tgcttaggca caggattgat					60 ttgtcgcaat gattgacacg attccgcttg acgctgcgta aggtttttgt aattttacag					120 gcaaccttt attcactaac aaatagctgg tggaa					155

<210> SEQ ID NO 15
<211> LENGTH: 22
<212> TYPE: DNA
<213> ORGANISM: Artificial Sequence
<220> FEATURE:
<223> OTHER INFORMATION: Forward PCR Primer for miox Coding Region

<400> SEQUENCE: 15
atgaaagttg atgttggtcc tg					22

<210> SEQ ID NO 16
<211> LENGTH: 18
<212> TYPE: DNA
<213> ORGANISM: Artificial Sequence
<220> FEATURE:
<223> OTHER INFORMATION: Reverse PCR Primer for Miox Coding Region

<400> SEQUENCE: 16
ttaccaggac agggtgcc					18

<210> SEQ ID NO 17
<211> LENGTH: 21
<212> TYPE: DNA
<213> ORGANISM: Artificial Sequence
<220> FEATURE:
<223> OTHER INFORMATION: Forward PCR Primer for Udh Coding Region

<400> SEQUENCE: 17
atgaccacta ccccttcaa t					21

<210> SEQ ID NO 18
<211> LENGTH: 17
<212> TYPE: DNA
<213> ORGANISM: Artificial Sequence

```
<220> FEATURE:
<223> OTHER INFORMATION: Reverse PCR Primer for Udh Coding Region

<400> SEQUENCE: 18
tcagttgaac gggccgg                                              17
```